US012161509B2

(12) United States Patent
Couade et al.

(10) Patent No.: US 12,161,509 B2
(45) Date of Patent: Dec. 10, 2024

(54) ULTRASOUND IMAGING METHOD AND AN APPARATUS IMPLEMENTING SAID METHOD

(71) Applicant: SUPERSONIC IMAGINE, Aix-en-Provence (FR)

(72) Inventors: Mathieu Couade, Aix en Provence (FR); Jeremy Bercoff, Aix en Provence (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 172 days.

(21) Appl. No.: 16/331,043

(22) PCT Filed: Sep. 11, 2017

(86) PCT No.: PCT/EP2017/072784
§ 371 (c)(1),
(2) Date: Mar. 6, 2019

(87) PCT Pub. No.: WO2018/046740
PCT Pub. Date: Mar. 15, 2018

(65) Prior Publication Data
US 2019/0200965 A1 Jul. 4, 2019

(30) Foreign Application Priority Data
Sep. 12, 2016 (EP) ..................... 16306146

(51) Int. Cl.
*A61B 8/08* (2006.01)
*A61B 8/00* (2006.01)
(Continued)

(52) U.S. Cl.
CPC .............. *A61B 8/5246* (2013.01); *A61B 8/06* (2013.01); *A61B 8/145* (2013.01); *A61B 8/4488* (2013.01);
(Continued)

(58) Field of Classification Search
CPC ......... A61B 8/5246; A61B 8/06; A61B 8/145; A61B 8/4488; A61B 8/485; A61B 8/5207; A61B 8/54; A61B 8/085
See application file for complete search history.

(56) References Cited

U.S. PATENT DOCUMENTS

2003/0083578 A1* 5/2003 Abe ....................... A61B 8/485
600/447
2006/0084870 A1* 4/2006 Kim ....................... A61B 8/463
600/437
(Continued)

FOREIGN PATENT DOCUMENTS

EP 2 138 103 A1 12/2009
EP 0 034 004 A1 6/2016
(Continued)

OTHER PUBLICATIONS

Shaaban, "Real-time ultrasound elastography: Does it improve B-mode ultrasound characterization of solid breast lesions?", Mar. 2012 (Year: 2012).*
(Continued)

*Primary Examiner* — Ashley K Buran
*Assistant Examiner* — Brooke Lyn Klein
(74) *Attorney, Agent, or Firm* — NIXON & VANDERHYE

(57) ABSTRACT

An ultrasound imaging method for generating a visualization image includes an emission and reception step of interleaved ultrasound waves, a processing step during which the received sequences are processed for generating three images via three different process, an image combining step during which the visualization image is determined by combining the three images for simultaneously visualizing the results of all images process.

11 Claims, 5 Drawing Sheets

(51) Int. Cl.
*A61B 8/06* (2006.01)
*A61B 8/14* (2006.01)
(52) U.S. Cl.
CPC ............ *A61B 8/485* (2013.01); *A61B 8/5207* (2013.01); *A61B 8/54* (2013.01); *A61B 8/085* (2013.01)

(56) References Cited

U.S. PATENT DOCUMENTS

| | | | |
|---|---|---|---|
| 2008/0137921 A1* | 6/2008 | Simon | G06T 7/149 382/128 |
| 2009/0149750 A1* | 6/2009 | Matsumura | A61B 5/0053 600/438 |
| 2009/0177089 A1* | 7/2009 | Govari | G06T 7/13 600/453 |
| 2009/0234230 A1 | 9/2009 | Bercoff et al. | |
| 2010/0130861 A1* | 5/2010 | Shimazaki | A61B 8/5238 600/443 |
| 2010/0179413 A1* | 7/2010 | Kadour | A61B 8/463 600/443 |
| 2014/0039317 A1 | 2/2014 | Sato | |
| 2015/0005630 A1* | 1/2015 | Jung | A61B 8/468 600/437 |
| 2015/0164476 A1* | 6/2015 | Kong | A61B 8/5207 600/438 |
| 2015/0209012 A1* | 7/2015 | Oh | G01S 7/52071 600/443 |
| 2016/0249884 A1* | 9/2016 | Hashimoto | A61B 8/485 600/438 |
| 2017/0055956 A1* | 3/2017 | Osumi | A61B 8/4416 |
| 2018/0172811 A1* | 6/2018 | Mosegaard | G01S 15/8984 |

FOREIGN PATENT DOCUMENTS

| | | | |
|---|---|---|---|
| EP | 3034004 A1 | | 6/2016 |
| JP | 2008284287 A | * | 11/2008 |
| JP | 2012061075 A | * | 3/2012 |

OTHER PUBLICATIONS

English translation of Foreign Kato JP 2012061075 (Year: 2012).*
Translated Waki (2008284287) (Year: 2008).*
Dumont Douglas M et al: "Feasability of a ARFI/B-mode/Doppler system for real-time, freehand scanning of the cardiovascular system", Medical Imaging 2011: Ultrasonic Imaging, Tomography, and Therapy, SPIE, 1000 20th St. Bellingham WA 98225-6705 USA, vol. 7968, No. 1, Mar. 3, 2011 (Mar. 3, 2011), pp. 1-12, XP060009692, DOI: 10.1117/12.877841.
Marwa A Shaaban et al: "Real-time ultrasound elastography: Does it improve B-mode ultrasound characterization of solid breast lesions?", The Egyptian Journal of Radiology and Nuclear Medicine, Elsevier, Amsterdam, NL, vol. 43, No. 2, Feb. 11, 2012 (Nov. 11, 2012), pp. 301-309, XP028509527, ISSN: 0378-603X, [retrieved on Feb. 21, 2012], DOI: 10.1016/J.EJRNM.2012.02.002.
International Search Report, dated Dec. 12, 2017, from corresponding PCT/EP2017/072784 application.
Holländer et al., "Plane-Wave Compounding in Automated Breast vol. Scanning: A Phantom-Based Study", Ultrasound in Medicine & Biology, 2016, vol. 42, No. 10, pp. 2493-2503.

* cited by examiner

I1 (e.g. B-mode image)

I2 (e.g. elastography image)

I3 (e.g. flow image)

ULTRASOUND IMAGING METHOD AND AN APPARATUS IMPLEMENTING SAID METHOD

FIELD OF THE INVENTION

The present invention concerns an ultrasound imaging method for generating a visualization image of a region inside a medium, and an ultrasound imaging apparatus implementing said method.

BACKGROUND OF THE INVENTION

It is known to have an ultrasound method/apparatus that generates a visualization image that combines two images: a first b-mode image that reveals morphology structure of the medium, and a second flow image that reveals the vascularization in the medium. There are also two sorts of flow images, called "color flow" and "PW mode" depending on the method employed.

Elastography imaging now provides images of medium elasticity, such color images giving quantitative information on medium stiffness that can be relevant for cancer diagnostic.

However, the color flow images and color elastography images are provided separately during two different ultrasound images exam, and relationship between tissue vascularization and tissue elasticity is impossible.

OBJECTS AND SUMMARY OF THE INVENTION

One object of the present invention is to provide an ultrasound imaging method for generating a visualization image of a region inside a medium, wherein the method comprises:
- an emission and reception step during which a plurality of emitted sequences of ultrasound waves are emitted inside a medium, a plurality of received sequences of ultrasound waves are received by a probe, said emitted and received sequences being temporally interleaved,
- a processing step during which the received sequences are processed for generating a first image via a first process, a second image via a second process and a third image via a third process, and wherein the first process, the second process and the third process are different one to the other,
- an image combining step during which the visualization image is determined by combining the first, second and third image for simultaneously visualizing the results of first, second and third process.

Thanks to these features, the method combines three types of images into a visualization image, the three images being taken in a quasi-simultaneous way inside the medium. The user can identify the relationship between the three types of images.

Such method reduces the examination time and improves the diagnostic accuracy.

Moreover, some of the taken images can be process with the same data from the plurality of received sequences, which improves the accuracy of relationships.

Then, improvements of the visualization image is made possible by various tuning of images combination.

In various embodiments of the method, one and/or other of the following features may optionally be incorporated:

According to an aspect, the second and third images are superposed over the first image.

According to an aspect, the first image is in grey scale, and the second and third images are in color scale with different color ranges.

According to an aspect, the second and/or third image comprises an outline with a predetermined and unique line property.

According to an aspect, the first process is b-mode ultrasound imaging, the second process is an elastography ultrasound imaging, and the third process is flow process imaging.

According to an aspect, the first, second and third processes have various time periodicity.

According to an aspect, the steps are repeated for periodically generating a visualization image that is updated over time.

According to an aspect, at least one of the received sequences is used by the second and third processes to process the corresponding second and third images.

According to an aspect, at least one of the emitted sequences is a sequence generating an unfocussed ultrasound wave inside the medium.

According to an aspect, the unfocussed ultrasound wave is a plane wave.

According to an aspect, the visualization image comprises:
- one view in which the first image is included, and
- a box having a size lower than the one of the view so as to be totally included inside said view, and wherein
  the first image fills said one view,
  the second image is superposed over the first image inside the box, and
  the third image is superposed over the second image inside the box.

According to an aspect, the second image is superposed with a first opacity property, and the third image is superposed with a third opacity property, the third opacity property being higher than the second opacity property.

According to an aspect, the visualization image comprises:
- a first view in which the first image is included,
- a first box having a size lower than the one of the first view so as to be totally included inside said view,
- a second view in which the first image is included, and
- a second box having a size lower than the one of the second view so as to be totally included inside said view, wherein
the first image fills each one of the first and second views,
the second image is superposed over the first image inside the first box, and
the third image is superposed over the first image inside the second box.

According to an aspect, the first and second views are organized vertically or horizontally inside the visualization image.

Another object of the invention is to provide an ultrasound imaging apparatus implementing the above method, said apparatus comprising:
- a probe for generating the plurality of emitted sequences and acquiring the plurality of received sequences,
- an electronic unit for controlling the probe,
- a processing unit for controlling the electronic unit, for processing signals from the received sequences so as to generate the first, second and third images, and for generating the visualization image on the bases of said first, second and third images.

BRIEF DESCRIPTION OF THE DRAWINGS

Other features and advantages of the invention will be apparent from the following detailed description of some of its embodiments given by way of non-limiting example, with reference to the accompanying drawings. In the drawings.

MORE DETAILED DESCRIPTION

Figure 1:
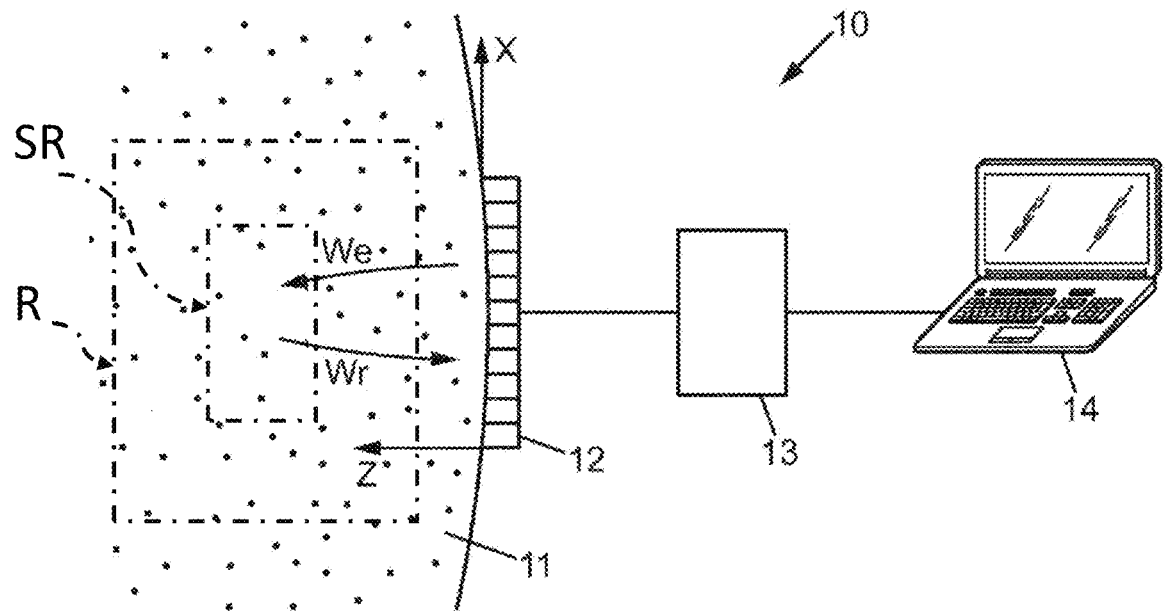
FIG. 1 is a schematic drawing of an apparatus implementing the ultrasound imaging method according to the invention.

FIG. 1 shows an apparatus 10 for implementing the method of the invention, for instance for the purpose of generating a visualization image corresponding to a region R inside a medium 11 and/or a sub-region SR included inside the region R.

The medium 11 is for instance a living body and in particular human or animal bodies, or can be any other biological or physic-chemical medium (e.g. in vitro medium). The volume of medium comprises variations in its physical properties. For example, the medium may comprise tissues and blood vessels, each one having various physical properties. For example, the tissue may comprise an area suffering from an illness (e.g. cancerous cells), or any other singular area, having various physical properties in comparison to other area of the medium. Some portions of the medium 11 may include some added contrast agent (e.g. micro bubbles) for improving the contrast of physical properties of these portions.

The apparatus 10 may include:
- a probe 12 comprising one ultrasound transducer or a plurality of ultrasound transducers (a transducer array), each transducer 12a being adapted to transform a signal into an ultrasound wave (emit) and/or to transform an ultrasound wave into a signal (receive),
- an electronic unit 13 controlling the transducers in the probe in both mode (receive and/or emit), and
- a processing unit 14 for controlling the electronic unit 13, for processing the signals by various processes, and for generating images and visualization images of the medium.

In a variant, a single electronic device could fulfil all the functionalities of the electronic unit 13 and of the processing unit 14. The processing unit 14 may be a computer.

The probe 12 can comprise a curved transducer so as to perform an ultrasound focussing to a predetermined position in front of the probe. The probe 12 can comprise a linear array of transducers, few tens of transducers (for instance 100 to 300) juxtaposed along an axis X so as to perform ultrasound focussing into a bi-dimensional (2D) plane. The probe 12 can comprise a bi-dimensional array so as to perform ultrasound focussing into a tri-dimensional (3D) volume.

The processing unit 14 comprises a processor 14a, a memory 14b containing instruction codes for implementation of the method and containing data concerning the method, a keyboard 14c and a display 14d for displaying images and/or visualization images.

The apparatus 10 can determines images inside the medium 10 of a region R and a sub-region SR, said sub-region being included inside the region R, as it will be explained later.

Figure 2:
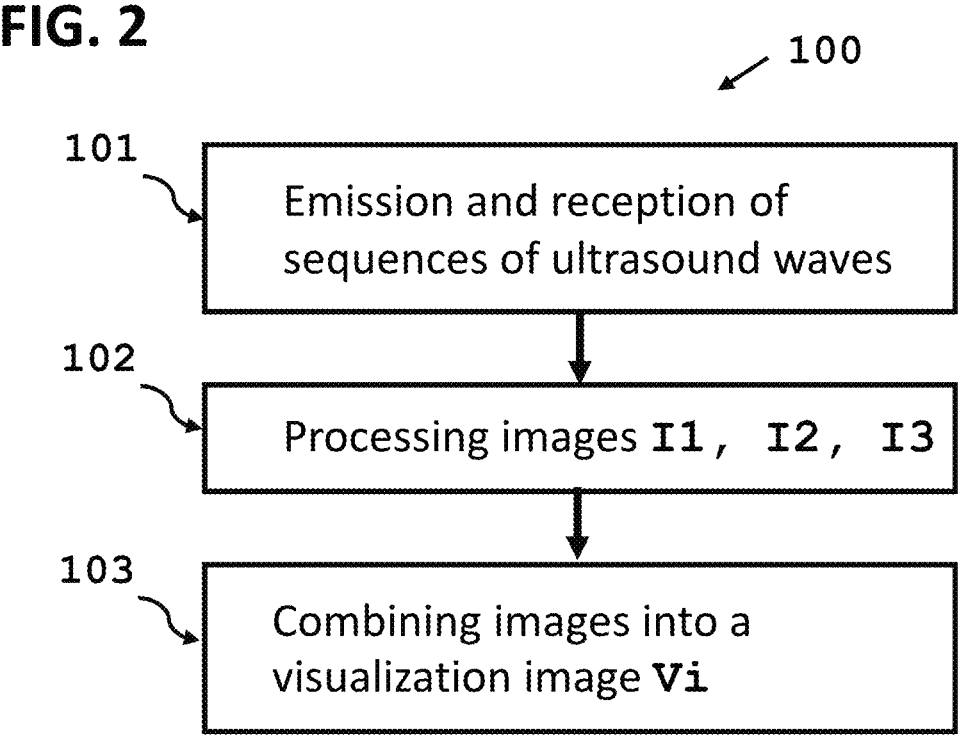
FIG. 2 is a flowchart presenting a general view of the ultrasound imaging method according to the invention.

The method 100 for generating a visualization image, according to the invention, is illustrated on FIG. 2, and this method mainly comprises the following steps:
- an emission and reception step 101 for emitting and receiving received sequences,
- a processing step 102 adapted to process the received sequences to generate three images, and
- an image combining step 103 adapted to combined the tree images into a visualization image.

The method is now more detailed.

During the emission and reception step 101, the processing unit 14 controls the electronic unit 13 so as a plurality of emitted sequences of ultrasound waves are emitted by the probe 12 inside the medium 11. The medium 11 then diffuses and reflects said ultrasound waves according to its content and echo ultrasound waves propagate back to the probe 12. Then, a plurality of received sequences of ultrasound waves (echo) are received by the probe 12.

The emitted and received sequences are temporally interleaved, and each received sequence corresponds to a (known) emitted sequence.

During the processing step 102, the processing unit 14 processes the received sequences for generating:
- a first image I1 via a first process,
- a second image I2 via a second process, and
- a third image I3 via a third process.

In present case, the first, second and third processes are different one the other ones, so as to generate three different images with a set of data (received sequences).

Figure 3:
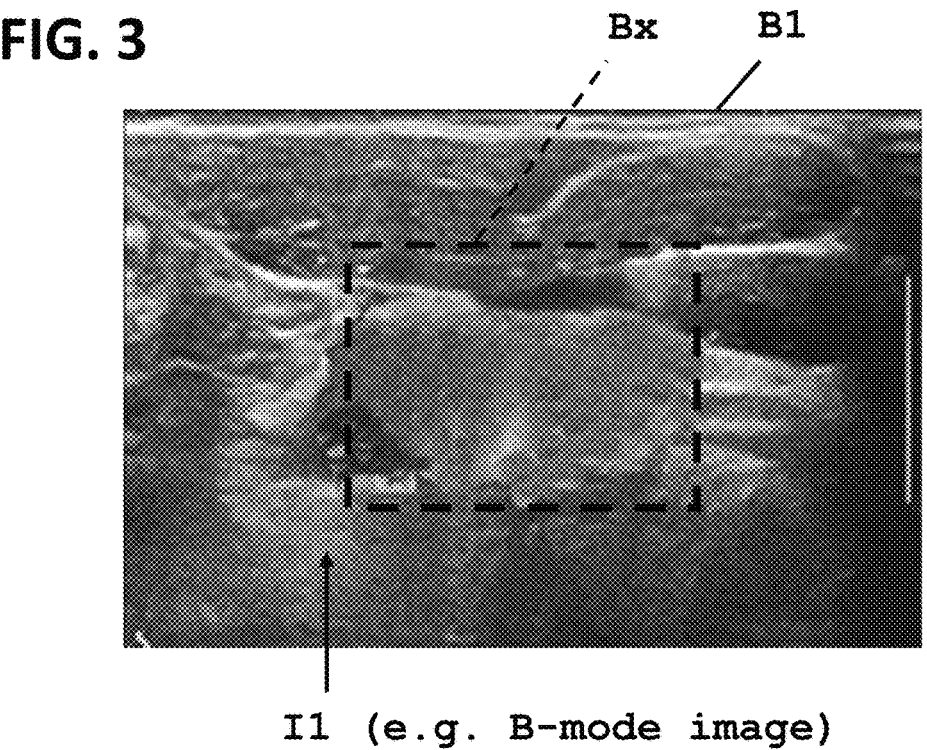
FIG. 3 is an example of first image.
Figure 4:
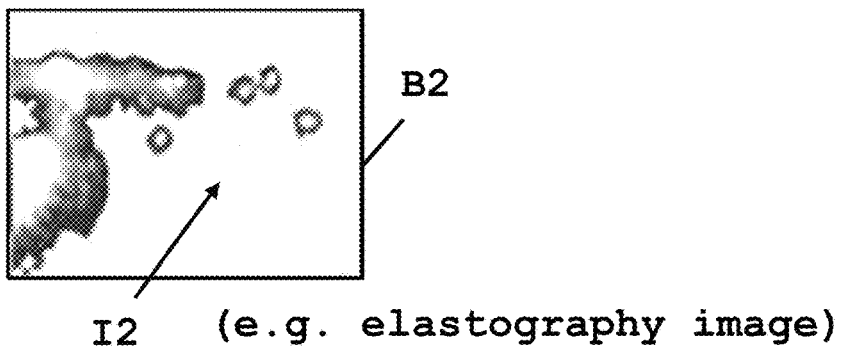
FIG. 4 is an example of second image.
Figure 5:
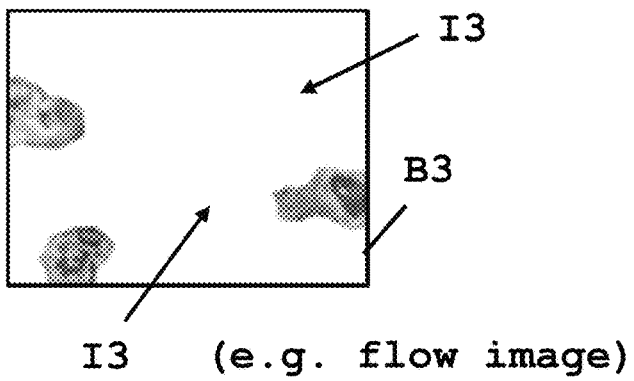
FIG. 5 is an example of third image.

In a preferred example:
- the first image I1 is a b-mode image that represents the intensity reflection of ultrasound wave in the medium 11 (as represented on FIG. 3), and therefore the morphology inside the medium; such image is determined by a first process, a b-mode process;
- the second image I2 is an elastography image that represents the rigidity or stiffness inside the medium 11 (as represented on FIG. 4); such second image is determined by a second process, an elastography process; and
- the third image I3 is a flow image that represents the flow inside the medium 11, for example for visualizing flow of blood in vessel, and therefore vascularization inside the medium (as represented on FIG. 5).

Various b-mode process, elastography process and flow process are well known for ultrasound imaging. For example, ones can refer to patent application US 2009/234230 for a fast elastography method.

The emitted sequences of ultrasound waves during the emission and reception step 101 must correspond to the ones that have to be used for the three images process (b-mode, elastography and flow).

The first image I1 may be in gray scale (as such scale is usually used for a b-mode image).

The second and third images I2, I3 may be in color scales, i.e. a range of predetermined colors. The color scales of second and third images have different colors: they do not overlap, i.e. they do not have common color, so that the second and third images I2, I3 can be easily distinguished one to the other, and can be distinguished from the grey scale of first image I1.

These scales can be determined by user, and displayed in the visualization image, optionally together with scale's values for user understanding (e.g. rigidity values for elastography image scale, and flow speed values for flow image scale).

The second and/or third images I2, I3 may be limited to a predetermined range or threshold: a minimum and/or a maximum value (i.e. physical value of rigidity or speed). Then, the image is not a full image and the image pixels, that are eliminated, are not significant and are not displayed by having a transparent color.

Therefore, an outline can be added inside such image, the outline surrounding the significant pixels of the image. The outline of each image has a line property: for example, a color and/or a thickness and/or a pattern. The outline property of second image I2 is preferably different than the outline property of the third image I3, so that such images differs and can be identified.

This creates outlined image shapes filed with a predetermined color scale. The image shapes of second and third images I2, I3 can be identified: The pixel belonging to second or third image I2, I3 are easily recognized thanks to the various color scales and/or the various outlines.

During the image combining step 103, the processing unit 14 combines the first image I1, the second image I2 and the third image I3 into a visualization image Vi and displays this visualization image to the display 14d so as to simultaneously visualize the result of first process, second process and third process to the user of the ultrasound imaging apparatus 10.

The second and third images I2, I3 are for example superposed over the first image I1: The second image I2 overlays the first image I1. The third image I3 overlays the first image I1.

The superposition of all the images is coherent for the positions in the medium 11 corresponding to the pixels: the superposed pixels correspond to information for the same position inside the medium.

Advantageously, the first image I1 is determined for a wide area inside the medium, corresponding to the region R represented on FIG. 1. The second image I2 and the third image I3 are determined for a reduced area inside the medium 11, corresponding to the sub-region SR.

Therefore, a box Bx is defined inside the first image I1, its area corresponding to the pixels that are processed for second and third images I2, I3, and corresponding to the real points inside the sub-region SR inside the medium 11. The borders B2 and B3 of second and third images are positioned on the outline of box Bx during superposition.

Then, the first image I1 that represents a general view of the medium, and wherein the user can recognize the organs, surrounds the first and second images I2, I3. This helps to understand the second and third images, and notably, this helps to link a specific zone in the second and/or third image to the position and type of organ inside the medium 11.

The box Bx and second image I2 and third image I3 have for example a rectangular shape. But, they may have any identical shape.

According to a variant of this superposition, a first opacity property is used to overlay the second image on the first image so as the first image is viewed under the second image. A second opacity property is used to overlay the third image on the first image. An opacity property is a percentage of a second image on the first image: If the opacity property is 0%, the combination result only shows the first image. If the opacity property is 100%, the combination result only shows the second image.

The first and second opacity property may be different. The second opacity property may by higher than the first opacity property.

For example, the first opacity property is comprised between 40% to 60% to see the first image under the second image, and the second opacity is comprised between 80% and 100% (included). For example, the first opacity property is 50%, and the second opacity property is 100%. In such a way, the first image I1 can be seen under the second image I2, and the third image I3 can be clearly seen above all with a correct contrast.

Thanks to these features, the first, second and third images can be easily distinguished one to the other while being superposed so as to understand the link between the various information of these images.

The visualization image Vi can have various layouts and can include various additional elements that are now described by way of some examples.

Figure 6:
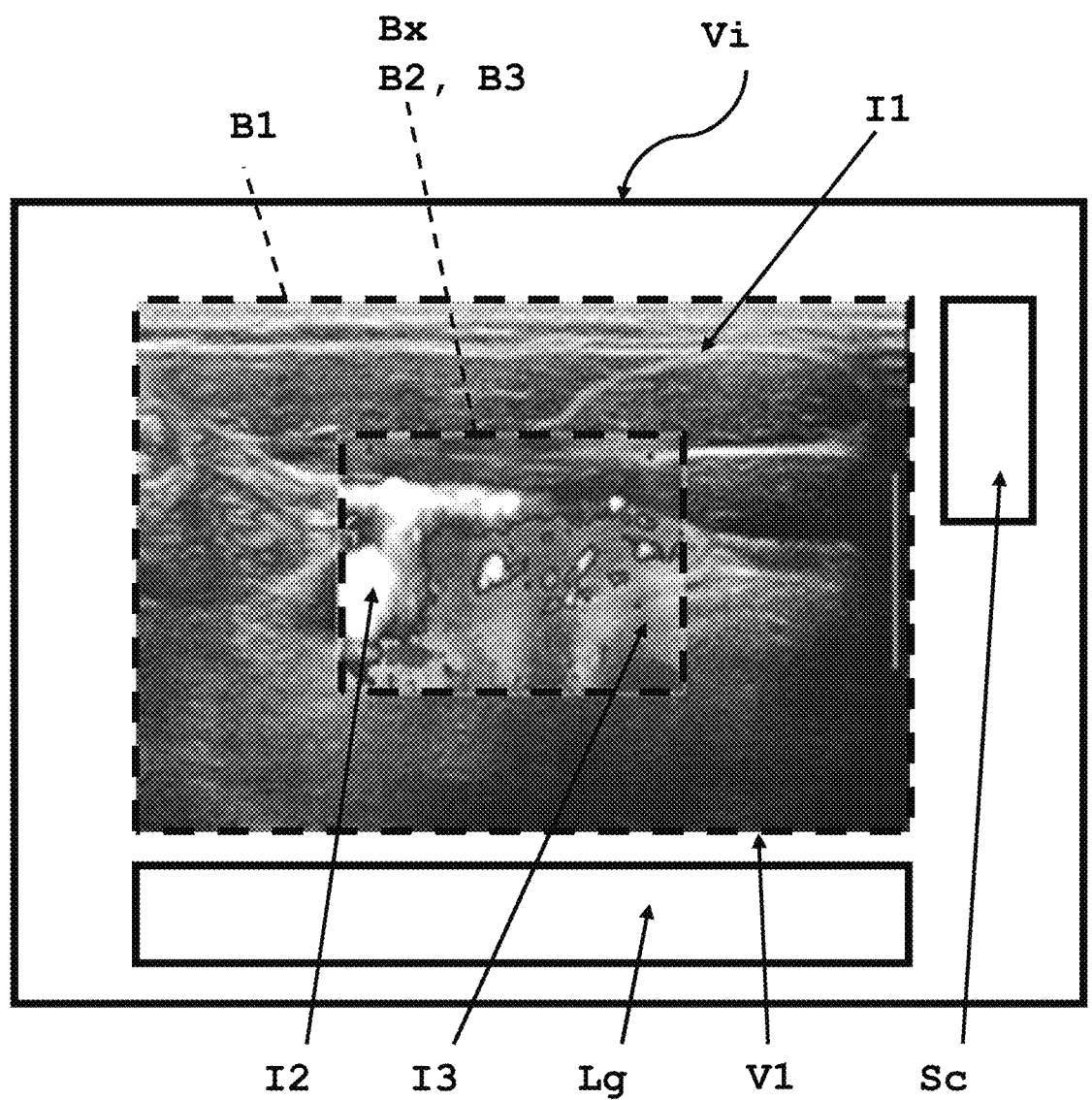
FIG. 6 is a first layout having one view for the visualization image provided by the method according to the invention.

In FIG. 6, a first example of schematic layout is represented. The visualization image Vi includes:
- a first view V1 (a first view frame) wherein the first image I1 having border B1 is included,
- a lateral area wherein scales Sc concerning the images inside the first view V1 are represented, and
- a lower area wherein legends Lg concerning the images inside the first view V1 are detailed.

The first image I1 comprises a box Bx wherein the second image I2 and the third image I3 are superposed (overlaid) as described above. The borders B2, B3 of the second and third images are also superposed over the box Bx, i.e. positioned on the outline of box Bx.

In the first view V1, the first, second and third images I1, I2, I3 are all superposed.

Figure 7:
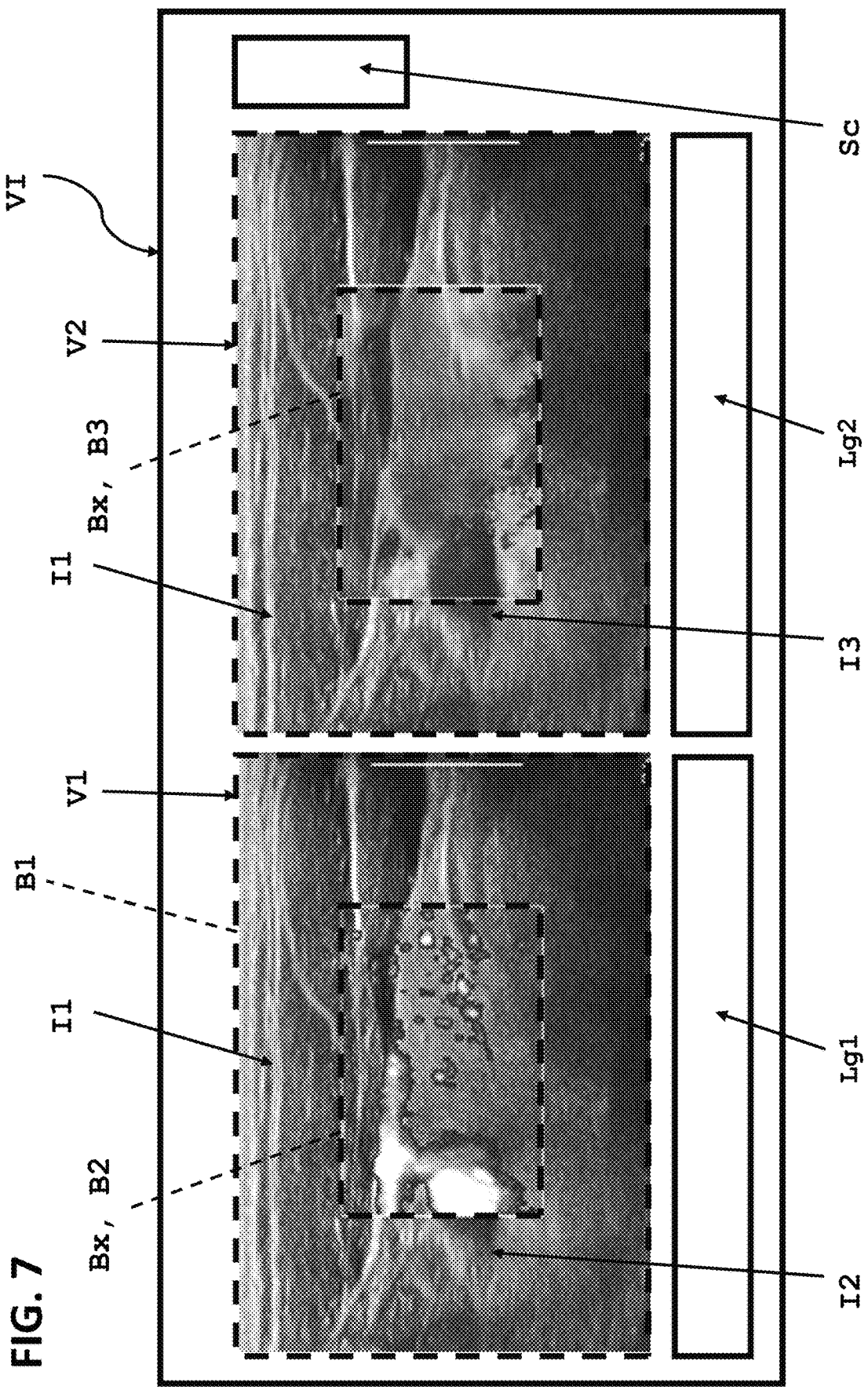
FIG. 7 is a second layout having two views for the visualization image provided by the method according to the invention.

In FIG. 7, a second example of schematic layout is represented. The visualization image Vi includes:
- a first view V1 (a first view frame) wherein the first image I1 having border B1 is included,
- a second view V2 (a second view frame) wherein the first image I1 having border B1 is also included,
- a lateral area wherein scales Sc concerning the images inside the first and second views V1, V2 are represented, and
- a lower area wherein legends Lg1, Lg2 concerning the images inside the first and second views V1, V2 are detailed.

In this example, the first and second views V1, V2 are side by side in a right-left configuration: The first view is on the left side of the visualization image Vi, and the second view is on the right side of the visualization image Vi.

The first image I1 in first view V1 comprises a box Bx1 wherein the second image I2 is superposed (overlaid) over the first image I1 of said view, as described above. The border B2 of the second image is also superposed over the box Bx1, i.e. positioned on the outline of box Bx1.

The first image I1 in second view V2 comprises a box Bx2 (preferably identical to the box Bx1 in the first view V1) wherein the third image I3 is superposed (overlaid) over the first image I1 of said view, as described above. The border B3 of the third image is also superposed over the box Bx2, i.e. positioned on the outline of box Bx2.

In the first view V1, the first and second images I1, I2 are superposed. In the second view V2, the first and third images I1, I3 are superposed. In some cases, such layout may be easier to understand for the user of the ultrasound device.

According to a third example (not represented), the visualization image Vi includes the same elements as in the second example of FIG. 7, but the first and second views V1, V2 are side by side in an upper-lower configuration: The first view is on the upper side of the visualization image Vi, and the second view is on the lower side of the visualization image Vi.

In the first view V1, the first and second images I1, I2 are superposed. In the second view V2, the first and third images I1, I3 are superposed. In some cases, such layout may be more comfortable, depending on the display sizes.

The emitted and received sequences are temporally interleaved, and each received sequence corresponds to a (known) emitted sequence.

Moreover, according to a preferred embodiment, image sequences adapted for generating the first, second and third images are also interleaved so as to reduce a time shift between these images. However, as each one requires a different frame rate FR (time interval between two consecutive image sequences for generating two consecutive images in time domain), interleave is predetermined taking into account these constraints for each image generation.

Figure 8:
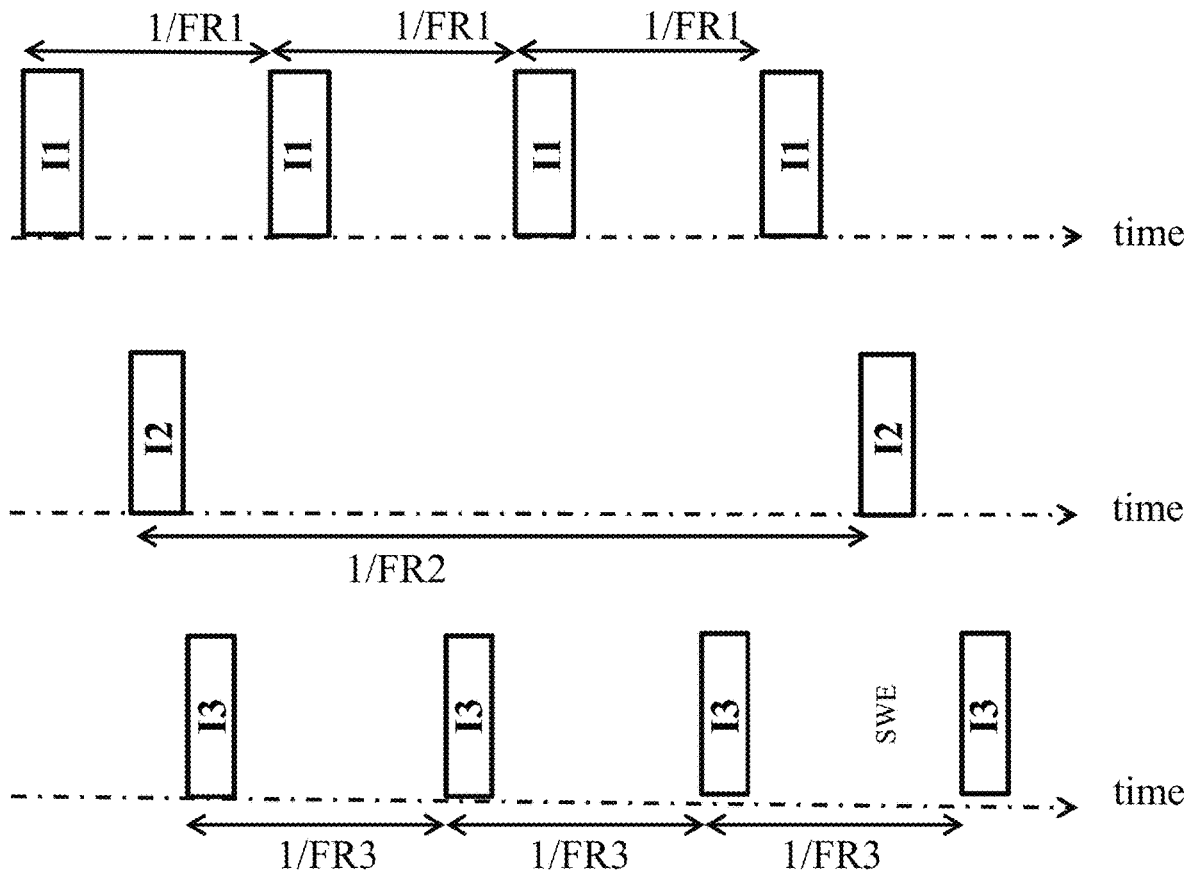
FIG. 8 is a first example of image sequence interleaving.

The FIG. 8 represents a first example of image sequences interleaving, wherein:
the first images I1 (b-mode images) are generated through a plurality of emitted and received sequences (rectangles with reference I1 inside); These sequences are repeated at a first frame rate FR1;
the second images I2 (elastography images) are generated through a plurality of emitted and received sequences (rectangles with reference I2 inside); These sequences are repeated at a second frame rate FR2;
the third images I3 (flow images) are generated through a plurality of emitted and received sequences (rectangles with reference I3 inside); These sequences are repeated at a third frame rate FR3.

In the represented FIG. 8, the first frame rate FR1 and the third frame rate FR3 are identical while the second frame rate is lower than the first and third frame rates.

Figure 9:
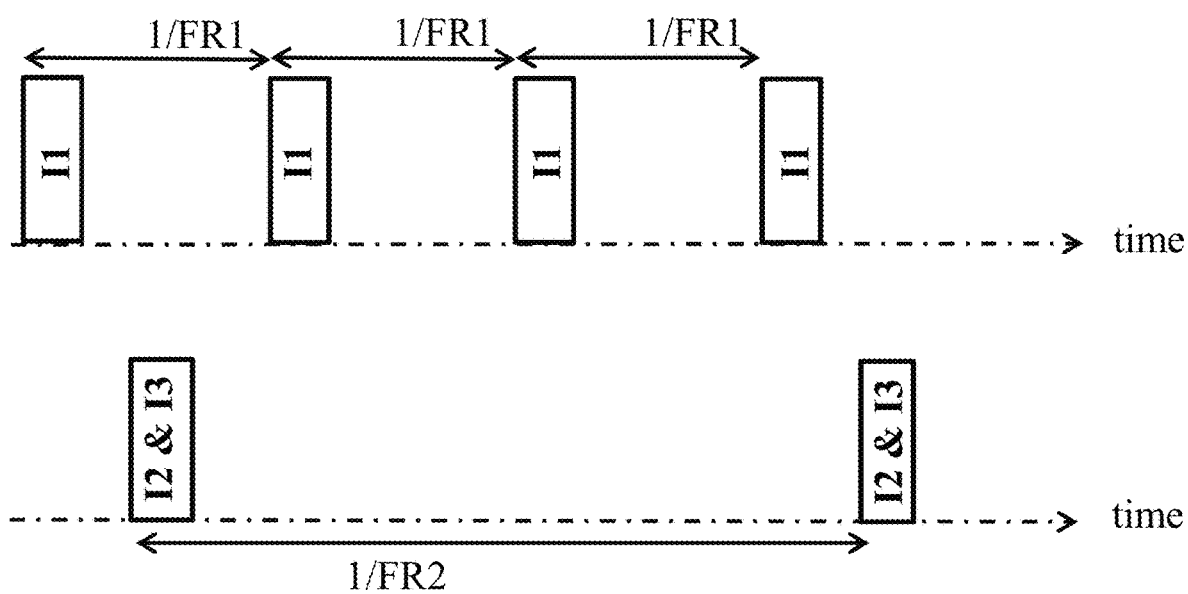
FIG. 9 is a second example of image sequence interleaving.

The FIG. 9 represents a second example of image sequences interleaving, wherein the second and third images I2, I3 are generated through the same plurality of emitted and received sequences (rectangles with reference I2&I3 inside); These sequences are repeated at a second frame rate FR3. Indeed, same sequences can be used to derive elastography and flow images: the same raw data memorized via the plurality of received sequences can be used to calculate both type of images.

As known, for e.g. by patent application US 2009/234230 the emitted and received sequences included inside an image sequence for second image (elastography image) can be composed of:
an emitted sequence of push waves adapted to generate a low frequency elastic wave, such as a shear wave (used for identifying elasticity inside the medium),
a plurality of emitted sequences of ultrasound unfocussed waves that are emitted inside the medium 11,
a plurality of received sequences resulting of said emitted sequences.

For ultrafast imaging the low frequency elastic wave, the plurality emitted sequences of unfocussed waves may be a plurality of plane waves, having a plurality of angle of inclination of said plane waves: There are a number N of tilted plane waves.

The second image process (elastography process) sums coherently the received sequences as explained in the reference patent application US 2009/234230.

Such method can apply to any image sequence interleaving, such as presented on FIGS. 8 and 9.

As proposed, the second and third processes (elastography and flow imaging process) can be combined and use same emitted and received ultrasound waves saved in memory as raw data.

A first step (a beamforming step) consists in reconstructing images (depth×width×frames) from per channel data (time samples×channels×acquisitions number). The number of frames does not necessary equal to the number of acquisitions as a single frame can be reconstructed from a set of transmit-receive events.

The beamformed image is noted img(x,n) where x denotes spatial coordinates and n the index of the reconstructed image.

A second step combines the reconstructing images.

For flow process using the above unfocussed waves, the method may implement a spatial temporal filtering step during which, after beamforming, so as to differentiate tissue motion from flow motion. The spatial temporal filtering step may be performed by a singular value decomposition SVD technique.

The spatial temporal filtering step then comprises the following sub-steps:
calculating the singular value decomposition SVD of the beamformed images that are organized in a two dimensional matrix (space versus time), as $$[U,S,V]=svd(img(x,n))$$

selecting some of the calculated vectors by a singular threshold value, and
filtering the images by using the selected calculated vectors, via a reconstruction operation:

$$img_{filt}(x,n) = \sum_{k \in List} s_k U(k,t) V(k,x)$$

Where List corresponds to the selected vectors.

The singular threshold value can be determined by different parameters. For example:
a fixed number or percentage of vectors, usually the first most energetic vector;
the singular value amplitude;
the variance of the temporal vectors;
the mean frequency of the Fourier transform of the temporal vectors;
detection of the maximal curvature point in the singular value energy curve.

The invention claimed is:

1. An ultrasound imaging method for generating a visualization image of a region inside a medium, the method comprising:
emitting a plurality of emitted sequences of ultrasound waves inside a medium and receiving a plurality of received sequences of ultrasound waves by a probe, said emitted sequences and the received sequences being temporally interleaved;
processing the received sequences to generate a first image via a first process, a second image via a second process, and a third image via a third process, the first process, the second process, and the third process being different from one another, the first process being b-mode ultrasound imaging, the second process being elastography ultrasound imaging, the third process being flow process imaging; and combining the first, second, and third images to simultaneously visualize results of the first, second, and third processes to determine the visualization image, wherein the first image is in grey scale, the second and third images are in color scale with different color ranges without overlap, the first image, the second image, and the third image being 2D images and being different types of images, wherein each of the second image and the third image is limited to a respective predetermined range 41 physical values respectively corresponding to the second image and the third image, each of the respective predetermined ranges having one or more of a minimum physical value and a maximum physical value, wherein pixels in the second image and the third image having physical values that are not inside the corresponding predetermined range of physical values are eliminated, the eliminated pixels not being displayed in the second image and the third image, remaining pixels, which have not been eliminated from the second image and the third image, are superposed on the first image to be displayed, the superposed pixels corresponding to information for the same position inside the medium, wherein the visualization image comprises:
  a view in which the first image is included, and
  a box having a size lower than the view to be totally included inside said view, wherein the first image fills said view,
the second image is superposed over the first image inside the box, and
the third image is superposed over the second image inside the box, and wherein the predetermined ranges of the second and third images are set so that the box includes at least one area in which only the first image is visible, without any portion of the second or third image displayed over the first image inside the at least one area.

2. The method according to claim 1, wherein the first, second, and third processes have various time periodicity.

3. The method according to claim 1, wherein the emitting and receiving, the processing, and the image combining are repeated to periodically generate a visualization image that is updated over time.

4. The method according to claim 1, wherein at least one of the received sequences is used by the second and third processes to process the corresponding second and third images.

5. The method according to claim 1, wherein at least one of the emitted sequences is a sequence generating an unfocussed ultrasound wave inside the medium.

6. The method according to claim 1, wherein the second image is superposed with a first opacity property, and the third image is superposed with a second opacity property, the second opacity property being higher than the first opacity property.

7. The method according to claim 1, wherein one or more of the second image and the third image comprise at least one outline with a predetermined and unique line property, said outline surrounding the remaining pixels, which are not eliminated, in the one or more of the second image and the third image in which the eliminated pixels are not displayed.

8. The method according to claim 5, wherein the unfocussed ultrasound wave is a plane wave.

9. The method according to claim 7, wherein the at least one outline comprises a plurality of outlines,
the second image comprises a first outline of the plurality of outlines surrounding the remaining pixels of the second image that are not eliminated,
the third image comprises a second outline of the plurality of outlines surrounding the remaining pixels of the third image that are not eliminated, and
the first and second outlines have different line properties.

10. An ultrasound imaging apparatus comprising:
a probe configured to generate a plurality of emitted sequences of ultrasound waves inside a medium and configured to acquire a plurality of received sequences of ultrasound waves, said emitted sequences and the received sequences being temporally interleaved;
a probe controller configured to control the probe; and
a processor configured to control the probe controller, the processor configured to process signals from the received sequences to generate a first image via a first process, a second image via a second process, and a third image via a third process, the first process, the second process, and the third process being different from one another, the first process being b-mode ultrasound imaging, the second process being elastography ultrasound imaging, the third process being flow process imaging, the processor configured to combine the first, second, and third images to simultaneously visualize results of the first, second, and third processes to generate a visualization image of a region inside the medium, wherein the first image is in grey scale, the second and third images are in color scale with different color ranges without overlap, the first image, the second image, and the third image being 2D images and being different types of images, wherein each of of the second image and the third image is limited to a respective predetermined range of physical values respectively corresponding to the second image and the third image, each of the respective predetermined ranges having one or more of a minimum physical value and a maximum physical value, wherein pixels in the second image and the third image having physical values that are not inside the corresponding predetermined range of physical values are eliminated, the eliminated pixels not being displayed in the second image and the third image, and remaining pixels, which have not been eliminated from the second image and the third image, are superposed on the first image to be displayed, the superposed pixels corresponding to information for the same position inside the medium, wherein the visualization image comprises :
  one view in which the first image is included, and
  a box having a size lower than the one view to be totally included inside said view, wherein the first image fills said one view,
the second image is superposed over the first image inside the box, and
the third image is superposed over the second image inside the box, and wherein the predetermined ranges of the second and third images are set so that the box includes at least one area in which only the first image is visible, without any portion of the second or third image displayed over the first image inside the at least one area.

11. The apparatus according to claim 10, wherein one or more of the second image and the third image comprise an outline with a predetermined and unique line property, said outline surrounding the remaining pixels, which are not eliminated, in the one or more of the second image and the third image in which the eliminated pixels are not displayed.

\* \* \* \* \*